(12) United States Patent
Ferrantelli

(10) Patent No.: US 8,721,567 B2
(45) Date of Patent: May 13, 2014

(54) MOBILE POSTURAL SCREENING METHOD AND SYSTEM

(76) Inventor: Joseph Ralph Ferrantelli, New Port Richey, FL (US)

( * ) Notice: Subject to any disclaimer, the term of this patent is extended or adjusted under 35 U.S.C. 154(b) by 116 days.

(21) Appl. No.: 13/336,123

(22) Filed: Dec. 23, 2011

(65) Prior Publication Data

US 2012/0165648 A1 Jun. 28, 2012

Related U.S. Application Data

(60) Provisional application No. 61/427,286, filed on Dec. 27, 2010.

(51) Int. Cl.
*A61B 5/117* (2006.01)

(52) U.S. Cl.
USPC .......................................... 600/594; 382/128

(58) Field of Classification Search
USPC ........... 345/645–680; 382/128–132; 600/595, 600/473–480, 407–410, 594
See application file for complete search history.

(56) References Cited

U.S. PATENT DOCUMENTS

| | | | |
|---|---|---|---|
| 3,659,494 A | | 5/1972 | Philbrick et al. |
| 5,947,742 A | * | 9/1999 | Katayama .................... 434/247 |
| 6,231,527 B1 | * | 5/2001 | Sol ................ 600/595 |
| 6,411,275 B1 | | 6/2002 | Hedberg |
| 6,751,410 B1 | | 6/2004 | Stavely |
| 7,077,813 B2 | * | 7/2006 | Grace ........................... 600/594 |
| 7,335,167 B1 | | 2/2008 | Mummy |
| 7,478,009 B2 | | 1/2009 | Cabrera et al. |
| 7,683,915 B2 | * | 3/2010 | Gunji ............................ 345/619 |
| 7,742,073 B1 | | 6/2010 | Cohen-Solal et al. |
| 7,761,233 B2 | | 7/2010 | Schott et al. |
| 7,796,871 B2 | | 9/2010 | Park et al. |
| 7,796,872 B2 | | 9/2010 | Sachs et al. |
| 7,876,320 B2 | * | 1/2011 | Marugame .................... 345/420 |
| 8,209,240 B2 | * | 6/2012 | Ryu et al. ..................... 705/27.1 |
| 2003/0076408 A1 | | 4/2003 | Dutta |
| 2006/0072019 A1 | | 4/2006 | Stavely et al. |
| 2006/0203131 A1 | * | 9/2006 | Gunji ............................ 348/739 |
| 2007/0083384 A1 | | 4/2007 | Geslak et al. |
| 2007/0230829 A1 | | 10/2007 | Sirohey et al. |
| 2008/0009773 A1 | | 1/2008 | Harrison et al. |
| 2008/0030464 A1 | | 2/2008 | Sohm et al. |

(Continued)

OTHER PUBLICATIONS

International Preliminary Report on Patentability, PCT/US2011/067111 (Jan. 9, 2013).

(Continued)

*Primary Examiner* — Sanjay Cattungal
(74) *Attorney, Agent, or Firm* — Antonelli, Terry, Stout & Kraus, LLP.

(57) ABSTRACT

A mobile, hand-held communication device with a display screen and a camera is programmed to perform a postural screening method. An image of a patient is acquired on the display screen having an array of pixels. A pixel to distance ratio of the displayed image is determined. A postural displacement of the patient in the displayed image is calculated using the determined ratio. A gyroscope, accelerometer and/or a level of the device is used to level the camera before capturing the image with the camera. Reference lines are overlaid on the display screen and the image to enable alignment of the image. A reference line on the display screen is used for normalizing a known distance in the aligned image to a reference distance of a known number of pixels on the screen for determining the ratio.

15 Claims, 5 Drawing Sheets

(56) References Cited

U.S. PATENT DOCUMENTS

| | | |
|---|---|---|
| 2008/0044169 A1 | 2/2008 | Wernersson |
| 2009/0046140 A1 | 2/2009 | Lashmet et al. |
| 2009/0262989 A1* | 10/2009 | Kozakaya .................... 382/118 |
| 2010/0002015 A1* | 1/2010 | Handa .......................... 345/650 |
| 2010/0077857 A1 | 4/2010 | Ye |
| 2010/0078479 A1 | 4/2010 | Epshteyn |
| 2011/0251903 A1* | 10/2011 | Ryu et al. ................... 705/14.73 |

OTHER PUBLICATIONS

International Search Report and Written Opinion, PCT/US2011/067111, Apr. 25, 2012.

* cited by examiner

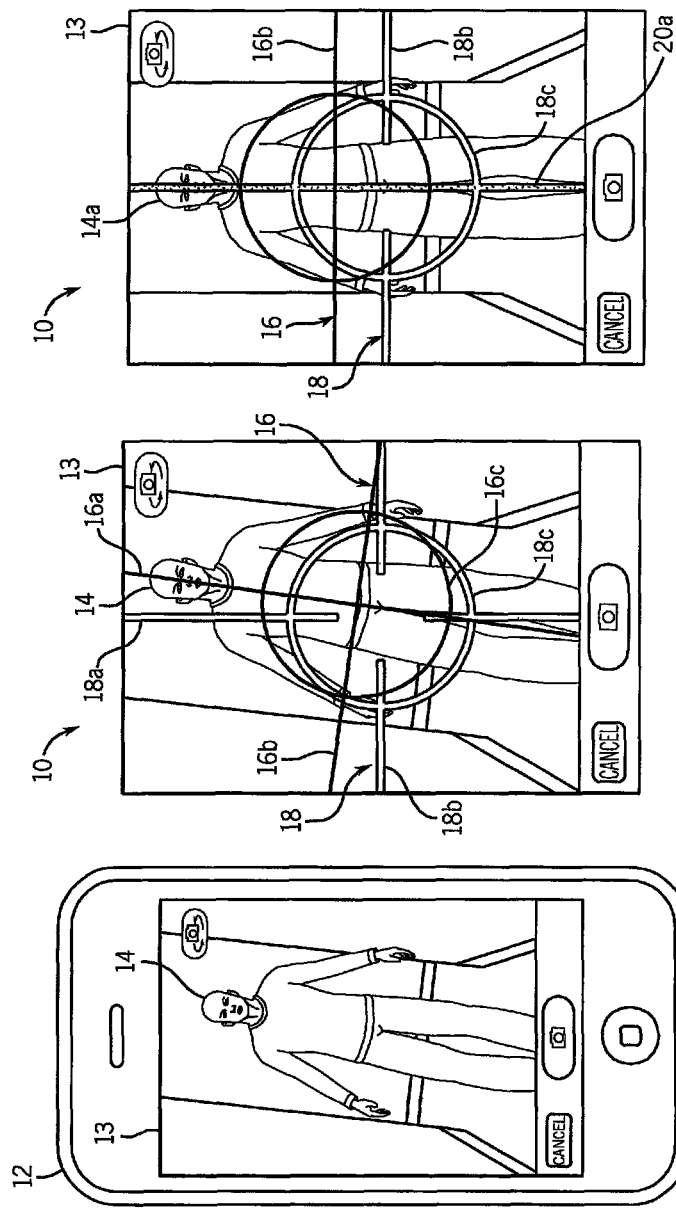

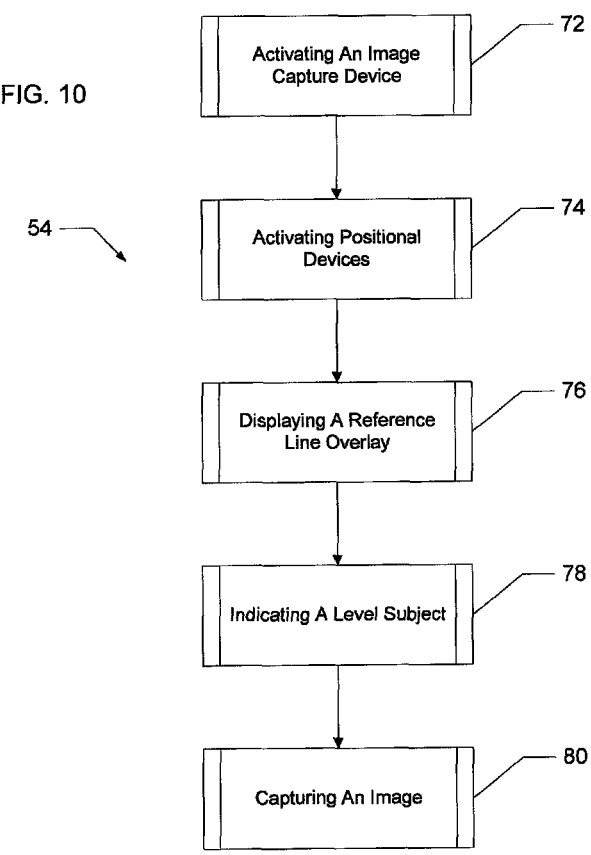

MOBILE POSTURAL SCREENING METHOD AND SYSTEM

RELATED APPLICATION

This application claims priority under 35 U.S.C. §119 of U.S. provisional application No. 61/427,286 filed Dec. 27, 2010. The entire disclosure of the provisional application is incorporated herein by reference.

TECHNICAL FIELD

The present invention concerns an improved postural screening method and system which according to example embodiments, enable screening a patient quickly and conveniently using only a mobile, hand-held communication device programmed according to the present invention.

BACKGROUND AND SUMMARY

A known postural screening method involves a person/patient standing in a framework between a vertical plumb line and a vertically oriented, planar backdrop having a grid-work of vertical and horizontal lines. The medical practitioner performing the screening then observes postural deviations (malalignments) of the patient in the frontal plane, sagittal plane and transverse plane relative to the vertical and horizontal lines on the backdrop and the plumb line. The postural deviations observed are then recorded on a postural evaluation chart. The data from the postural evaluation can be input to a computer to aid in analysis in selection of a corrective exercise program, for example. U.S. Pat. No. 7,077,813 discloses such a system and method.

Drawbacks of the known method and system include that taking all the postural deviation measurements can be time consuming and imprecise. The screening must also be conducted in a facility having the required framework of vertical backdrop and plumb line. The known method and system are not readily movable and the method is not capable of being performed in another setting lacking these components. There is a need for an improved, mobile postural screening method and system which overcome these drawbacks and limitations. The present invention addresses this need.

The improved postural screening method according to the example embodiments of the present invention comprises acquiring an image of a patient on a display screen having an array of pixels, determining a pixel to distance ratio for the displayed image, and calculating a postural displacement of the patient in the displayed image using the determined ratio. The standing framework of vertical backdrop and plumb line of the prior art is not necessary. According to the disclosed method, a known linear distance in the displayed image and the number of display screen pixels spanning the distance are used in determining pixel to distance ratio. The known linear distance in an example embodiment is the height of the patient. Alternately, or in addition as a secondary calibration, a marked distance can be provided in the acquired image of the patient, as by the use of a meter stick in the image or other markings of a known distance apart, to provide a known linear distance.

The postural screening method in example embodiments further includes scaling the size of the image relative to the display screen to normalize the known linear distance in the image to a display screen reference distance corresponding to a known number of pixels for determining the pixel to distance ratio. According to a disclosed method, at least one reference line is provided over the displayed image to demark the display screen reference distance.

The method as disclosed herein further includes displaying a reference line overlaid on the screen providing vertical, horizontal and center references, providing a corresponding reference line anchored to the displayed patient's image, and adjusting the image in the display so that the two reference lines are aligned before determining the pixel to distance ratio.

The patient's image can be acquired by accessing a database. Alternatively, the person performing the screening can operate an image capture device of a camera for acquiring the image of the patient. The method preferably includes leveling the image capture device before capturing the image from which the pixel to distance ratio is to be determined for eliminating distortion. According to the example embodiments, the image capture device and display screen are part of a mobile, hand-held communication device having at least one positional device selected from the group consisting a gyroscope, an accelerometer, and a level. The method includes activating the at least one positional device and using an output thereof to provide a reference for leveling the image capturing device.

In disclosed embodiments, the method further includes displaying a reference line on the display screen over the acquired image, performing panning to center the image on the screen, and performing zooming to fit the image in the reference line before determining the pixel to distance ratio. Still further, the method comprises providing anatomical landmarks on the acquired image of the patient to facilitate calculating a postural displacement. The display screen is a touch screen for this purpose to identify coordinates for calculation of postural displacements by the programmed computer of the mobile, hand-held communication device.

A system for performing postural screening according to the invention comprises means for acquiring an image of a patient on a display screen having an array of pixels, means for determining a pixel to distance ratio for the displayed image and means for calculating a postural displacement of the patient in the displayed image using the determined ratio. The means for acquiring an image of a patient according to an example embodiment includes an image capture device of the mobile, programmed, hand-held communication device. Preferably, the device includes at least one positional device selected from the group consisting of a gyroscope, an accelerometer, and a level which provides a reference for leveling the image capturing device. The system further includes means for panning a displayed image on the screen to center the image on the screen, and means for zooming to fit a displayed image in a reference line on the display screen. Means are provided for displaying at least one reference line over the displayed image to demark a display screen reference distance corresponding to a known number of pixels for determining the pixel to distance ratio.

The system of the disclosed embodiments further includes means for displaying a reference line overlaid on the screen providing vertical, horizontal and center references, means for displaying a corresponding reference line anchored to the displayed patient's image, and means for aligning image and display screen reference lines before determining the pixel to distance ratio. The system further includes means for providing anatomical landmarks on the acquired image of the patient to facilitate calculating a postural displacement.

The present invention further includes a machine-readable medium containing at least one sequence of instructions that, when executed, causes a machine to: calculate at least one postural displacement of a patient from a displayed image of the patient on a display screen having an array of pixels, using a determined pixel to distance ratio for the displayed image.

These and other objects, features and advantages of the invention will become more apparent from the following detailed description of example embodiments taken with the accompanying drawings.

BRIEF DESCRIPTION OF DRAWINGS

FIG. 1 is a front perspective view of a mobile communication device with an image capturing device in the form of a camera, not shown, on the back side of the device for acquiring an image of a patient and, as shown, a display screen on the front opposite side having a two-dimensional array of pixels on which the image as seen on the camera is displayed.

FIG. 2 is a front perspective view of the screen of the device of FIG. 1 showing a step of the postural screening method wherein a reference line is overlaid the image providing vertical, horizontal and center references on the display screen and wherein a corresponding reference line is anchored to the displayed patient's image.

FIG. 3 is a front perspective view of the screen of the device of FIG. 1 showing another step of the postural screening method wherein the two reference lines in FIG. 2 have been aligned in the vertical or sagittal plane by rotation of the device relative to the patient being viewed by the camera.

FIG. 10 is a process flow diagram of acquiring an image of a patient with the device of FIG. 1.

DETAILED DESCRIPTION

The following detailed description taken with the accompanying drawings is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention generally provide a postural screening method comprising acquiring patient information, acquiring an image of a patient, displaying a reference line overlaid on the acquired image for scaling the acquired image, providing panning to center the acquired image, providing zooming to fit the image within the displayed reference lines, for normalizing the patient's height, determining a pixel to distance ratio using the acquired patient information and the normalized patient height, calculating postural displacements, and presenting a postural analysis. Aspects of the present invention provide a postural screening method that may be implemented on a mobile, hand-held communication device that incorporates the device's gyroscope, accelerometer, and camera.

Referring now to FIG. 1, a front perspective view of a mobile, hand-held communication device 12 is shown, which on one side has a screen 13 capable of displaying a frontal image 14 of a patient being viewed with a camera or image capture device on an opposite side. The device in the embodiment is an Apple iPhone 4 the computer of which is programmed in accordance with the invention as described hereinafter to perform the disclosed postural screening method. Other mobile, hand-held communication devices capable of running a program in accordance with the invention could also be used, such as iPad, Android devices including tablets and Windows based tablets. FIGS. 2-8 show front perspective views of screen 13 showing steps of a posture screening method according to an embodiment of the present invention. Reference will be made to FIGS. 1-8 in the foregoing description of the postural screening method.

Figure 4:
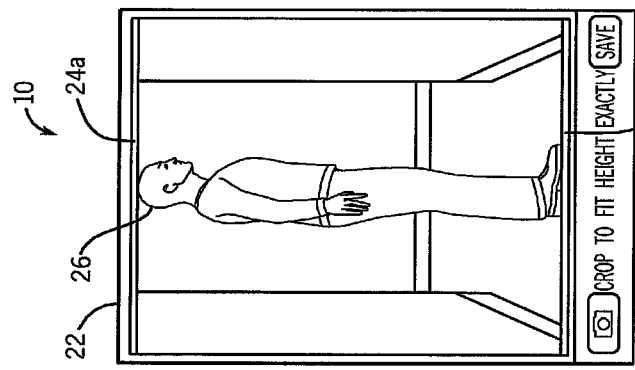
FIG. 4 is a front perspective view of the screen of the device of FIG. 1 showing a further step of the postural screening method wherein the two reference lines in FIG. 3 have been aligned in the vertical plane by tilting the device at the top toward the patient to level the image capturing device.
Figure 5:
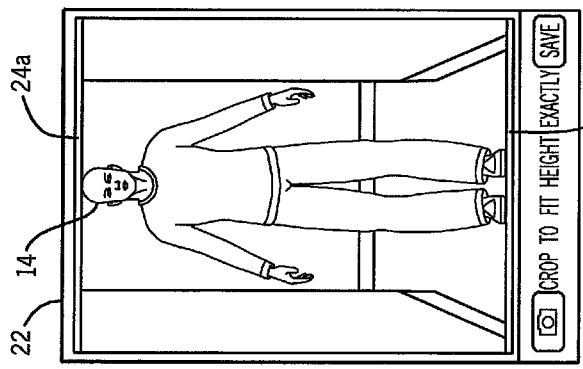
FIG. 5 is a front perspective view of the screen of the device of FIG. 1 showing another step of the postural screening method wherein two spaced horizontal lines are displayed on the screen at the top and bottom and the image has been centered by panning and scaled by zooming with the camera to fit the image precisely in the reference distance defined between the two lines to normalize the height of the image to a screen distance corresponding to a known number of pixels spanning the distance in the vertical direction.
Figure 6:
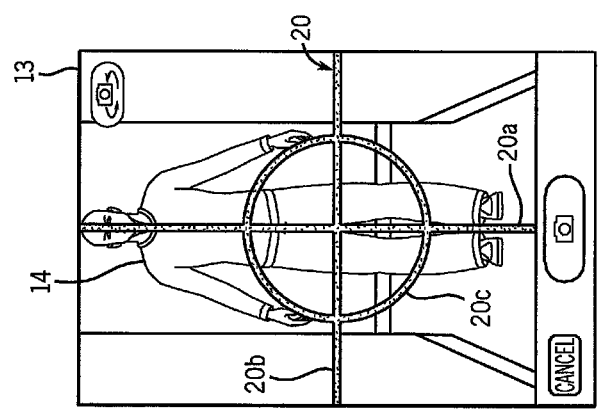
FIG. 6 is a front perspective view of the screen of the device of FIG. 1 showing an image of the patient like that of FIG. 5 but in the direction of the frontal plane of the patient.
Figure 8:
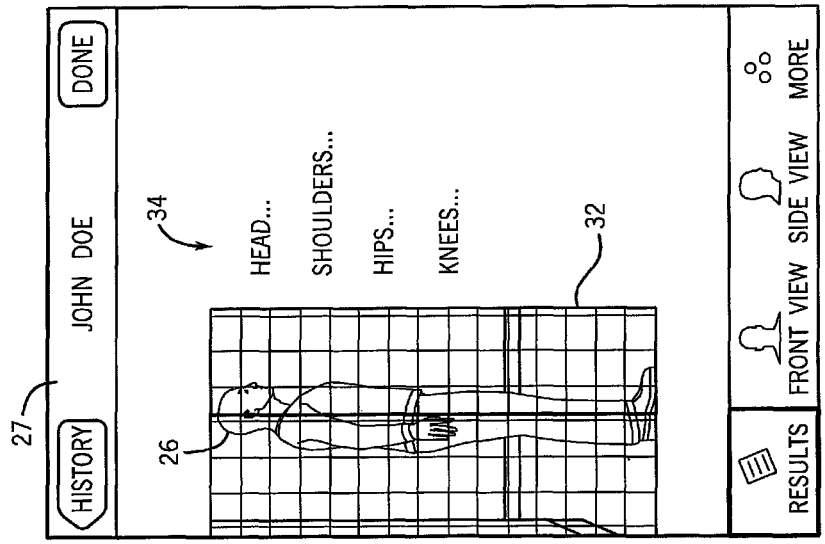
FIG. 8 is a front perspective view of the screen of the device of FIG. 1 wherein the image acquired in FIG. 6 optionally is displayed behind a grid overlay of vertical and horizontal lines against which a qualitative view of postural displacement is observed.
Figure 7:
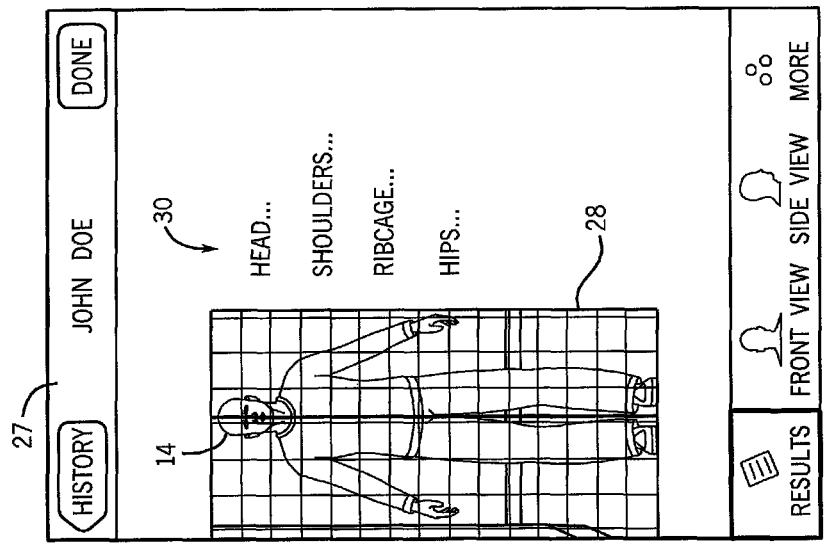
FIG. 7 is a front perspective view of the screen of the device of FIG. 1 wherein the image acquired in FIG. 5 optionally is displayed behind a grid overlay of vertical and horizontal lines against which a qualitative view of postural displacement can be observed.
Figure 9:
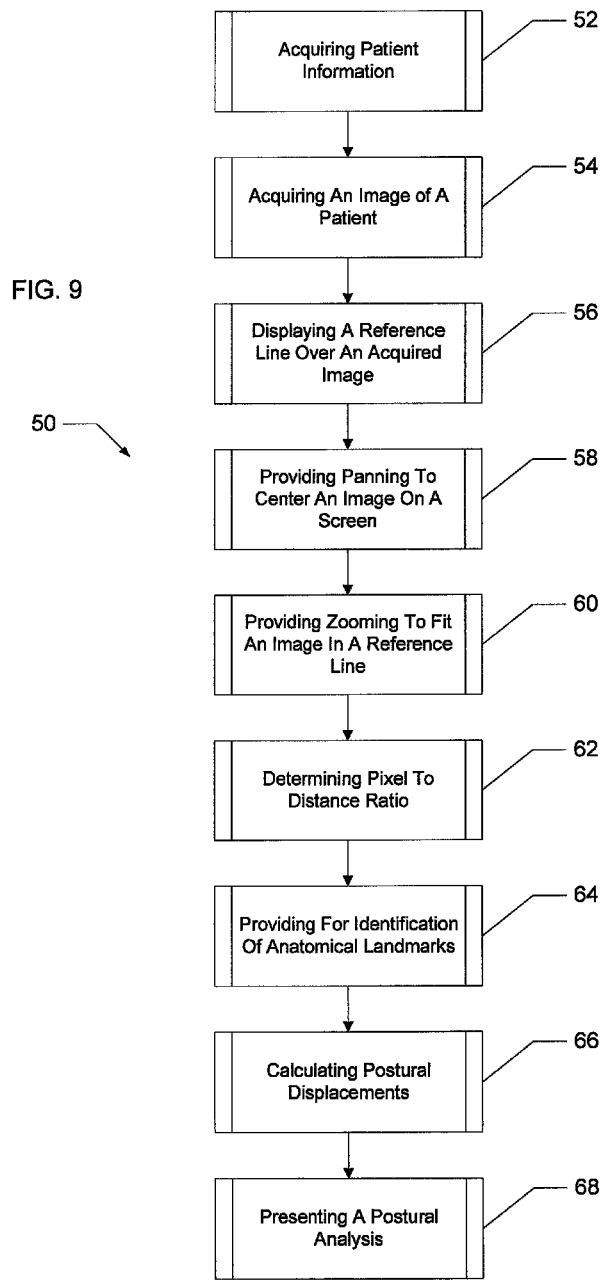
FIG. 9 is a process flow diagram of a method of postural screening according to an example embodiment of the present invention.

Referring now to FIG. 9, a postural screening method 50 is shown according to an embodiment of the present invention. Method 50 in the example embodiment includes a step 52 of acquiring patient information, which may include, for example, accessing a database or prompting a user to enter information. Acquired information in may include, for example, height, weight, sex and age of a patient.

Method 50 may include a process 54 of acquiring an image of the patient. Referring now to FIG. 10, a process flow diagram of process 54 of acquiring a frontal image 14 of the patient is shown. Process 54 as disclosed includes a step 72 of activating an image capture device, in this case the camera of the iPad 4. Process 54 in the embodiment includes a step 74 of activating a positional device, namely one or more of a gyroscope, an accelerometer, and a level in the device. The positional device(s) is used in accordance with the present invention to provide feedback to a user as to whether the image capture device is level.

Process 54 includes a step 76 of displaying a reference line overly 18 on screen 13. The reference line overlay 18 may aid a user in aligning the patient in the field of view of the image capture device by providing, for example, a vertical reference 18a, a horizontal reference 18b, and a center reference 18c. Process 54 includes a step 78 if indicating a level patient. According to the embodiment of the present invention, in step 78 a visual indication including, for example, corresponding references 16a, 16b, and 16c, are provided anchored to frontal image 14. An aligned frontal image 14 may have a reference line 20, which may have vertical, horizontal, and center reference lines 20a, 20b, and 20c, which may, for example, change colors indicating alignment. Process 54 may also include a step 80 of capturing an image, for example, once alignment is achieved. In an exemplary embodiment of the present invention, a plurality of images may be acquired including, for example, frontal image 14, lateral image 26, and a rear perspective image.

According to a variation of the embodiment of the present invention, process 54 may include accessing a data storage device. The data storage device may include, for example, a picture roll or album, which may contain a previously captured image of the patient.

Referring again to FIG. 9 method 50 may include a step 56 of displaying an upper reference line 24a and a lower reference line 24b over a display 22 of frontal image 14 and a lateral image 26 of the patient. The two spaced parallel lines are spaced apart a reference distance corresponding to a known number of pixels of screen 13. The displayed reference lines 24a and 24b may be used as a reference for aligning or normalizing the images 14 and 26, which may require positioning or scaling. Hence, method 50 may include a step 58 of providing panning capability of the acquired image to a user, and a step 60 of providing zoom capability of the acquired image to a user. The provided panning capability may allow a user to properly center or rotate images 14 and 26 to fit in reference lines 24a and 24b. The provided zoom capability may allow a user to properly size an acquired image to fit it within reference lines 24a and 24b for normalizing the height of the patient in the acquired image and establishing a pixel height of the patient. Method 50 may include a step 62 of determining a pixel-to-distance ratio, which may be a quotient calculated by dividing a pixel height of images 14 and 26 divided by a patient's height.

Method 50 may include a step 64 of providing for identification of the patient's anatomical landmarks, wherein a user may be prompted to identify locations of a plurality of anatomical landmarks on the acquired image of the patient by touching the touchscreen of the device to identify an anatomical landmark. The plurality of the landmarks may correspond, for example, to skeletal landmarks, bone markings, or joints. The identified plurality of landmarks may be used with the known pixel to distance ratio for the displayed image to calculate absolute distances and relative spatial positioning thereof, and may be used in an analysis of the patient's posture. In an exemplary embodiment of the present invention, the selection of anatomical landmarks may be on a plurality of images 14 and 26.

Method 50 in the embodiment includes a step 66 of calculating postural displacements using the determined pixel to distance ratio. The displacements may include, for example, linear displacements and angular displacements. Method 50 may include a step 68 of presenting a postural analysis 27. Postural analysis 27 may display, for example, the calculated linear or angular displacements 30, 34 and any deviation thereof from a normal or proper posture taking into account, for example, the patient's age, sex, height, and weight. The normal or proper posture itself can be displayed over the displayed patient's image to provide a visual comparison.

Requirements of the mobile, hand-held communication device, the software, and the interaction therebetween, and specific operations or steps of the program for achieving the described functions of the method for an example embodiment are set forth below.

Leveling
Orientation Tracking

Requires an environment that can provide real-time or near real-time horizontal and vertical orientation readings. These readings may be provided by an "accelerometer".

1. Begin reading the orientation data from the accelerometer.
2. Track each reading in a historical array of readings; do not discard old readings.
3. When more than one reading has been tracked, apply a low-pass filter against the newest and the historical readings. This will provide accelerometer readings that more accurately reflect the constant effects of gravity and reduce the influence of sudden motion to the accelerometer.

Head-Up Display (HUD) Overlay

Requires a camera and a display screen that renders the camera's current view. Requires an application programming interface that allows drawing and displaying images over the camera view on the display screen, partially obscuring portions of the camera view. Finally, requires a pre-drawn graphic image files. The graphic image file may be partially transparent with one or more simple horizontal and vertical lines drawn on the image. The image file may also be more complex with circles, swirls, targets, multiple horizontal and vertical lines, etc. The image file will be used twice: once as stationary reference, once as dynamically moving indicator. While only one image is required the visual design may be more appealing using two image files, one for each usage.

1. Initialize the camera and viewpoint through normal methods of those devices.
2. Using the programming interface and apply the image to the display screen.
3. Using the programming interface, adjust the image location so the image is viewable on the display screen. The camera display screen should render both the camera's current view and the image file. This image application will not be modified further and serves the purpose of a stationary reference.
4. Using the programming interface and apply the image to the display screen, again.
5. Using the programming interface, adjust the image location in the exact same manner as the stationary image.
6. Using the programming interface, instruct the display to draw the second image over the first stationary image.
7. The camera display screen should render the camera's current view with both the image files drawn over the camera view, partially obstructing the camera view.
8. The second image's location will be modified later and serves the purpose of a movement indicator.

User Feedback—Leveling the Camera

Requires both the Orientation Tracking and the HUD Overlay methods described above. Orientation readings may be assigned x, y, and z planes which are discussed here as "roll", "pitch", and "yaw".

1. Using the "roll" reading from the accelerometer, apply a rotation to the movement indicator image of the HUD. The programming interface of the display screen overlay will dictate the angle units (i.e. radians, degrees) required to rotate the movement indicator image. Use common angle mathematics to convert the reading to radians or degrees as required.
2. Use the programming interface to apply a standard mathematic rotation matrix to the movement indicator image's coordinate system.
3. The movement indicator image should render partially rotated on the camera display screen.
4. Using the programming interface or the operating system documentation, determine the screen coordinates for the camera display (for example, the iPhone 4S device boasts 960×640 pixel display, however the iOS operating system assigns the size of 320×460; interest here is in the operating system size of 320×460; the operating system will handle conversion between the device display 'space' and the operating system 'space').
5. Using the programming interface or the accelerometer documentation, determine the minimum and maximum values of the accelerometer "pitch" readings (for example, the iOS operating system provides "pitch" readings as fractional decimal in the range of −1.00 through +1.00).
6. Using the programming interface, read the current location coordinate of the center of the movement indicator image.
7. Add or subtract the pitch reading to the vertical location coordinate, restricting the value to the maximum and minimum boundaries of the screen coordinates.
8. Using the programming interface, apply the the result of the addition (subtraction) to the movement indicator image.
9. The movement indicator image should be rendered on the camera display screen in a different location. The image's center point should remain within the viewable area of the display screen.
10. The software should continuously monitor the readings of the accelerometer. With each new reading, update the rotation and location coordinates of the movement indicator image as shown above.
11. With one image stationary and a complimentary image moving, the user will be able to visually notice when the image perfectly overlap one another in both location and rotation. This registration is their feedback that the device is oriented correctly.

Display and Physical Measurements
Cropping

Requires a software environment that provides visual display elements (views) that can be nested inside of one another; allowing one element to surround or envelope another. For example, the iOS operating system provides the UIView element (including UIView derivatives). For real-time cropping, requires a display screen that renders the views and any changes to the views (including size, scale, rotation, color, brightness, etc)
1. Create two views, nested inside one another.
2. Load an image into the software (from a camera, disk drive, computer memory, etc)
3. Using the programming interface to assign the image to the inner view.
4. Optionally, use the programming interface to scale the inner view to be larger than the outer view.
5. Optionally, use the programming interface to adjust the location of the views so the inner view's boundaries extend past the outer view equally in all directions.
6. Regardless of completing step 4 and 5, allow the user to manipulate the inner view's size, scale, and location while keeping the outer view fixed in both size, scale, and location. Manipulation may occur by tracking the user input through any computer input device. For example, on the iOS operating system manipulation could be tracked by custom touch-screen readings or standard pinch-and-zoom features.
7. After user manipulation has completed (indicated by an arbitrary user action or input; for example pressing a "Done" button) use the programming interface to read the current size and position of both the inner and outer views.
8. Use the programming interface to capture the portion of the inner view image that is currently within the outer view's boundaries. Any portion of the inner view that extends past the outer view's boundaries will be cropped and discarded.
9. The programming interface may require the cropping boundary to be pre-calculated. The cropping boundary is used by the programming interface and applied to the original image to produce a new image from a portion of the original. The cropping boundary can be calculated with simple arithmetic:
   calculate (or read from the programming interface) the final offset distance between the inner view and outer view's center points,
   calculate (or read from the programming interface) the final resizing scale applied to the inner view,
   use the offset divided by the scale to determine the origin of the cropping boundary
   use the fixed size of the outer view divided by the scale to determine the dimensions of the cropping boundary
   For example, the X coordinate of a cropping boundary calculated in the iOS operating system would be: x=outerview.contentOffset.x/outerview.zoomScale; and the width of the cropping boundary would be:

width=outerview.frame.width/outerview.zoomScale;

As an example of calculating the cropping boundary, assume the following:
   An image of size 460×460
   An outer view of size 300×400
   The user has manipulated the inner image view to move it an arbitrary direction and scaled to be twice as large. The result of the manipulation is an image with effective size of 920×920 (×2 scale) with an offset of 195 in the X coordinate direction and 289 in the Y coordinate.
   The X coordinate of the cropping box would be 195/2=97.5 and the width of the cropping box would be 300/2=150.
   For reference, the Y coordinate in this example would be 144.5 and the height 200.
   The programming interface should produce a new image from the region of the original image with top left corner at 97.5, 144.5, width of 150 and height of 200.

Pixel Distance

Requires an image of an object cropped in a manner that the top and bottom of the object are at the edges of the top and bottom of the image, and the physical height of the object must be known. Requires a software environment that can interpret image data and provide pixel dimensions of the image.
1. Load the image into the software (from a camera, disk drive, computer memory, etc)
2. Use the programming interface to read the pixel height of the image
3. Divide the known height of the object by the pixel height reading to determine the ratio of pixels to physical distance
4. The ratio can be used to calculate and convert any distance of pixels to physical distances by multiplying the ratio and the pixel distance For example, given an image that is 1000 pixels in height and an object that is known to be 60 inches in height we can calculate:
   Each pixel represents 0.06 physical inches: 60/1000=0.06
   A distance of 250 pixels represents 15 physical inches: 0.06×250=15

It should be understood, of course, that the foregoing relates to exemplary embodiments of the invention and that modifications may be made without departing from the spirit and scope of the invention as set forth in the following claims.

The invention claimed is:

1. A postural screening method using a mobile, programmed, hand-held communication device including a display screen, a camera for acquiring an image of a patient on the display screen, and at least one positional device selected from the group consisting of a gyroscope, an accelerometer, and a level, the method comprising:
    displaying an image on the display screen of the camera's current view of a patient,
    utilizing the at least one positional device of the mobile, programmed, hand-held communication device to level the camera,
    capturing an image of the patient once the camera is leveled,
    determining a pixel to distance ratio for the displayed image,
    calculating a postural displacement of the patient in the displayed captured image using the determined ratio.

2. The method of claim 1, wherein a known linear distance in the displayed captured image and the number of display screen pixels spanning the distance are used in determining the pixel to distance ratio.

3. The method of claim 2, wherein the known linear distance is the height of the patient.

4. The method of claim 2, wherein the known linear distance is a marked distance provided in the acquired image of the patient.

5. The method of claim 2, including scaling the size of the image relative to the display screen to normalize the known linear distance to a display screen reference distance corresponding to a known number of pixels for determining the pixel to distance ratio.

6. The method of claim 5, including providing at least one reference line over the displayed image to demark the display screen reference distance.

7. The method of claim 1, wherein said utilizing the at least one positional device includes providing a stationary reference line overlay on the display screen over the patient's image, providing a movement indicator overlay on the display screen over the stationary reference line overlay and the patient's image anchored to the displayed image for movement therewith as a function of orientation of the camera when tracked by the at least one positional device, and adjusting the orientation of the camera while tracking the orientation of the camera with the at least one positional device to align the movement indicator overlay with the stationary reference line overlay on the display screen to level the camera, wherein the stationary reference line overlay on the screen provides vertical, horizontal and center references, and wherein the movement indicator overlay anchored to the displayed patient's image provides corresponding references.

8. The method of claim 1, including providing anatomical landmarks on the displayed captured image of the patient to facilitate calculating a postural displacement.

9. The method of claim 1, including displaying a reference line on the display screen over the acquired image, performing panning to center the image on the screen, and performing zooming to fit the image in the reference line before determining the pixel to distance ratio.

10. A system for performing postural screening comprising:
    a mobile, programmed, hand-held communication device including
        a display screen having an array of pixels,
        a camera for acquiring an image of a patient on the display screen
        at least one positional device selected from the group consisting of a gyroscope, an accelerometer, and a level,
        means for utilizing the at least one positional device for leveling the camera,
        means for capturing an image of the patient once the camera is leveled,
        means for determining a pixel to distance ratio for the displayed image,
        means for calculating a postural displacement of the patient in the displayed image using the determined ratio.

11. The system of claim 10, including means for panning a displayed image on the screen to center the image on the screen, and means for zooming to fit a displayed image in a reference line on the display screen.

12. The system of claim 10, including means for displaying at least one reference line over the displayed image to demark a display screen reference distance corresponding to a known number of pixels for determining the pixel to distance ratio.

13. The system of claim 10, wherein the means for utilizing the at least one positional device for leveling the camera includes means for providing a stationary reference line overlay on the display screen over the image of the camera's current view of a patient, means for providing a movement indicator overlay provided on the display screen over the stationary reference line overlay and the image of the camera's current view of the patient anchored to the displayed image for movement therewith as a function of orientation of the camera tracked by the at least one positional device, and wherein the stationary reference line overlay on the screen provides vertical, horizontal and center references and wherein the movement indicator overlay anchored to the displayed image provides corresponding references.

14. The system of claim 10, including means for providing anatomical landmarks on the displayed captured image of the patient to facilitate calculating a postural displacement.

15. The system of claim 10, wherein the means for determining a pixel to distance ratio for the displayed image includes means providing a known linear distance in the displayed captured image and the number of display screen pixels spanning the distance.

* * * * *